United States Patent [19]
Jaeger

[11] Patent Number: 5,797,693
[45] Date of Patent: Aug. 25, 1998

[54] APPARATUS INTENDED FOR DISPENSING SUCCESSIVE ZONES OF A DISPOSABLE STRIP

[75] Inventor: Gérard Jaeger, Blonay, Switzerland

[73] Assignee: Asulab S.A., Bienne, Switzerland

[21] Appl. No.: 639,901

[22] Filed: Apr. 29, 1996

[30] Foreign Application Priority Data

May 2, 1995 [FR] France ................. 95 05224

[51] Int. Cl.[6] .......................... B01L 11/00; G01N 37/00
[52] U.S. Cl. ................................... 403/24; 74/527
[58] Field of Search .................. 74/527; 271/267, 271/266, 84; 403/24

[56] References Cited

U.S. PATENT DOCUMENTS

| | | | |
|---|---|---|---|
| 1,650,076 | 11/1927 | Laencher | 271/266 |
| 2,768,768 | 10/1956 | Cornell et al. | 74/527 X |
| 3,825,160 | 7/1974 | Lichtenberger et al. | 74/527 X |
| 4,233,734 | 11/1980 | Bies . | |
| 4,964,971 | 10/1990 | Riemann | 204/403 |
| 5,395,504 | 3/1995 | Saurer et al. | 204/403 |
| 5,525,297 | 6/1996 | Dinger et al. | 422/63 |

FOREIGN PATENT DOCUMENTS

| | | |
|---|---|---|
| 287054 | 10/1988 | European Pat. Off. . |
| 609760 | 8/1994 | European Pat. Off. . |
| 2710414 | 3/1995 | France . |

*Primary Examiner*—Anthony Knight
*Attorney, Agent, or Firm*—Sughrue, Mion, Zinn, Macpeak & Seas, PLLC

[57] ABSTRACT

An apparatus for dispensing multizone disposable testing strips which are inserted in the apparatus by a user. The apparatus has, for the strips (34), a circulation passage (29) in which a cursor (35) is able to slide, each strip being able to be coupled to the cursor. Ratchet members (54, 57, 62a to 65), associated with a driving member attached to the cursor, are arranged so as to enable the step by step movement of the cursor in the direction of the opening (28) of the passage (29) from any position in which the cursor can be, this being achieved via a direct driving of the cursor. Accordingly, it is always possible to bring the cursor back into a position where it is near said opening. The apparatus can be applied to object dispensing devices, such as medical tablets, or to blood sugar level measuring devices.

6 Claims, 7 Drawing Sheets

APPARATUS INTENDED FOR DISPENSING SUCCESSIVE ZONES OF A DISPOSABLE STRIP

BACKGROUND OF THE INVENTION

The present invention relates to a dispensing apparatus requiring the use of disposable elements in the shape of a strip to operate, each of these strips comprising in the longitudinal direction several successive utilisation zones intended to be detached from the strip after their use.

More particularly, the invention concerns an apparatus of this type forming a measuring device enabling a parameter of a substance deposited on successive zones of a strip forming a disposable measuring sensor, also called a multizone sensor, to be measured.

A measuring device of this type may advantageously be used for measuring blood sugar levels, for use by diabetics. Different aspects of such a device have been disclosed in several French patents filed in the name of the applicant and amongst which one may cite patent FR 93 01331 (corresponding to U.S. Pat. No. 5,395,504) as regards the electrochemical measuring method used, patent application FR 93 11316 (corresponding to U.S. Pat. No. 5,525,297) as regards a cutting device enabling the used measuring zones to be detached from the disposable strip, FR 93 11317 as regards an electrical connection device enabling the sensor strip to be connected to an electronic measuring circuit intended to elaborate the result of the measurement in a form intelligible to a user, and finally FR 93 11319 which concerns more specifically a device for ejecting the last section of the sensor strip, when all the measuring zones have been used.

Figure 1:
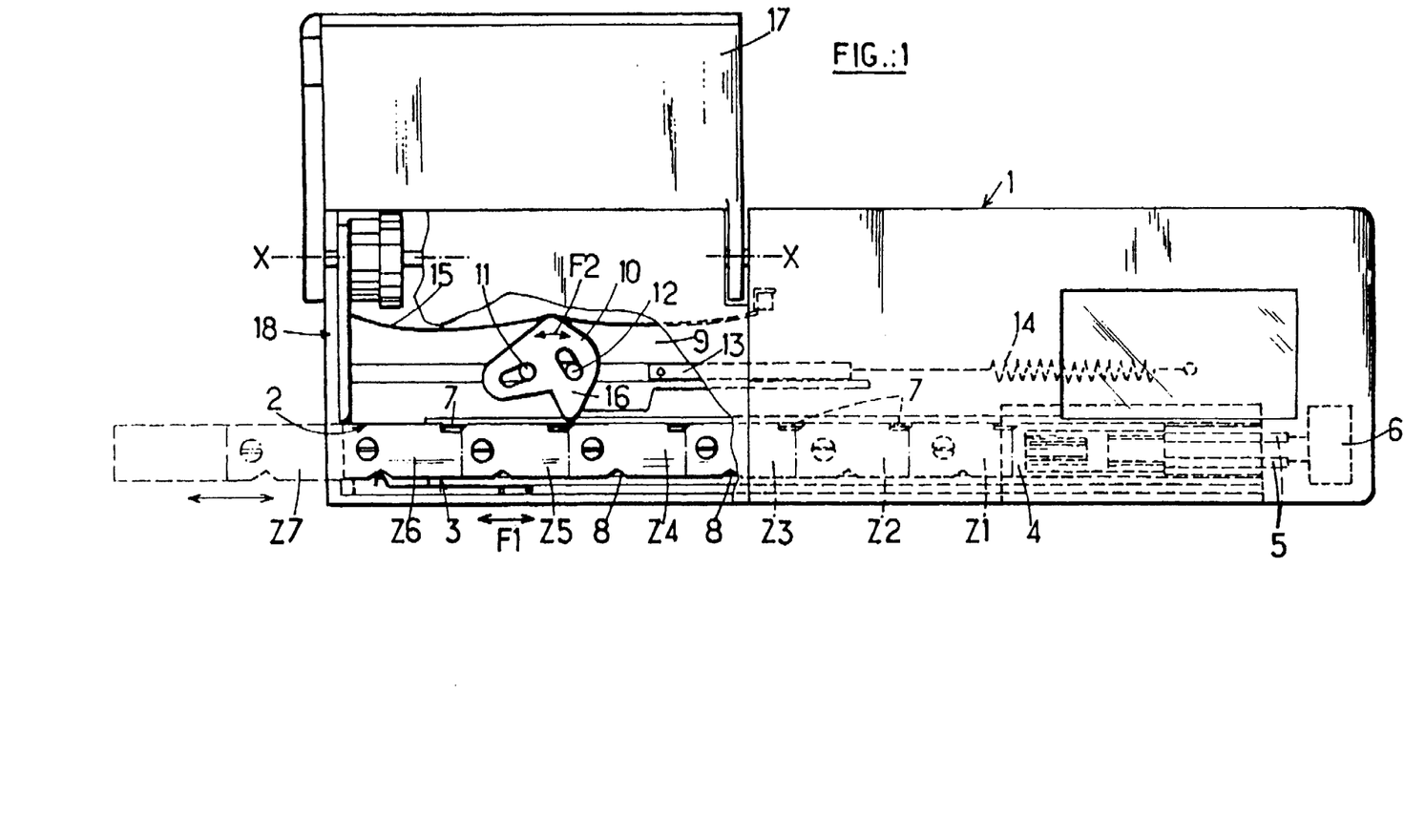
FIG. 1, already described, is a schematical plane view, partially cut away, of a dispensing apparatus according to the aforecited patent applications.

FIG. 1 of the attached drawings shows a measuring device in which one finds, in summary form, an embodiment example of the improvements which were the subject of the aforementioned patent applications, it being understood that in order to find a detailed description of them, one may refer to the texts of said patent applications.

Thus, the measuring device comprises a case 1, of a general elongated shape and of such a size that it can easily be held in the palm of an adult's hand. This case defines a circulation passage 2 longitudinally oriented in case 1 and intended for the circulation of a sensor strip 3 (double arrow F1) and a cursor 4. The latter is responsible for transmitting the electric signal coming from sensor strip 3 to electric lines 5 which extend along passage 2. These lines are in turn connected to an electronic circuit 6 intended to process this electric signal in a suitable manner to make it intelligible to a user by means of a display device which is also provided in case 1.

In the example of FIG. 1, sensor strip 3 is specifically adapted for measuring blood sugar levels. A detailed description of a strip of this type can be found in the first patent application cited above. One need only keep in mind here that it comprises several measuring zones, seven in this case referenced Z1 to Z7 of which zone Z7 shown in dotted lines is assumed already to have been used and detached from strip 3.

It will also be noted that the sensor strip comprises for each of zones Z1 to Z7 a forward feed catch 7 on one of its longitudinal edges and for each of the zones except zone Z7 a positioning notch 8 situated on the other edge of the strip.

Forward feed catches 7 co-operate with a longitudinal forward feed mechanism 9 of strip 3 along its passage 2.

The latter comprises a control button (not visible in FIG. 1) mounted so as to slide longitudinally in the case, that is to say as seen in FIG. 1, above passage 2.

2

The control button co-operates with a rotating latch 10 guided on two studs 11 and 12 which are attached to a bar 13. The latter is coupled to the control button and mounted so as to slide in case 1 in the direction of arrow F1 against the action of a return spring 14 fixed to case 1. Rotating latch 10 is held in a non active position (shown in FIG. 1) by a leaf spring 15 and comprises a central nose 16 intended to co-operate with forward feed catches 7 of sensor strip 3.

Thus, it is understood that when the control button is activated back and forth, the sensor strip moves forward the length of a measuring zone of the strip, the forward feed mechanism causing latch 10 to rotate in a reciprocating manner (along arrow F2) to first of all push the strip out of the passage by one step and then to return to the inactive position as shown by disengaging itself from the strip.

The device also comprises a cover 17 rotatably mounted on the case around an axis X—X and mechanically coupled to a cutting mechanism 18 enabling the disposable zone of the strip which has just been used to be cut, by a simple closing movement of cover 17.

It is also to be noted that cursor 4 slides freely in passage 2 and is pushed backwards when disposable sensor strip 3 is inserted. The latter is mechanically coupled during this insertion when cursor 4 abuts the bottom of passage 2. The cursor carries for this purpose an resilient coupling member which yields to the insertion force exerted on strip 3 by the user, in order to latch onto this strip as soon as the insertion force is released.

Operating tests of the measuring device which has just been described have shown that it functions satisfactorily and without difficulties as long as the sensor strip is used up gradually and no accident takes place such as for example the deterioration of one of its forward feed catches.

It is also possible for the user, distractedly, to engage a new strip in the case when there is already one in passage 2 which is not yet entirely used up. The user then pushes the old piece of strip, with the sliding contact which is coupled thereto, back into the bottom of the passage. However, the user, realising his error, will remove the new strip without being able to bring forward either the old piece or the cursor.

SUMMARY OF THE INVENTION

An aim of the invention is to provide a solution to the problem cited above.

The invention thus concerns a dispensing apparatus requiring the use of disposable elements having the shape of strips to operate, each of these strips comprising in the longitudinal direction several successive utilisation zones intended to be detached from the strip after their use, said apparatus comprising:

a case defining a circulation passage for said strips, said passage having, taking account of the direction in which said strips are introduced, an upstream end and a downstream end, a forward feed mechanism for bringing said strip out of the circulation passage in accordance with a step by step movement after its introduction into the latter by a user, a sliding unit mounted so as to move in said passage, operationally coupled to said forward feed mechanism and intended to be coupled to the downstream end of said strip when it is introduced by the user, and coupling means carried by said sliding unit and arranged so as to assure the coupling between the latter and said strip, said dispensing apparatus being characterised in that said sliding unit comprises a cursor mounted so as to slide in said circulation passage and provided with a driving member, said forward feed mechanism comprises ratchet means intended to co-operate with said driving member to assure said coupling and to enable the step by step forward feed of said cursor, and said ratchet means are coupled to a control button mounted freely in said case to enable said step by step movement to be controlled.

As a result of these features, the disposable strip is driven in accordance with the step by step movement via the sliding unit which is coupled thereto when it is inserted into the circulation passage, said sliding unit itself being engaged with the ratchet means provided in the case. The step by step movement thus becomes independent of the presence or absence of the disposable strip. The latter may thus be incomplete, or even deteriorated and despite this still be removed from the apparatus. Furthermore, the disposable strip does not have to be shaped in order to co-operate with the forward feed means. It may thus be simpler and one no longer needs to take account of the presence of driving catches or suchlike in determining its width.

Other features and advantages of the invention will appear during the following description, which is given solely by way of example and made with reference to the attached drawings in which:

DESCRIPTION OF THE PREFERRED EMBODIMENT

FIGS. 2 to 6 show a preferred embodiment of the dispensing apparatus according to the invention in its application to a device enabling blood sugar levels to be measured for use by diabetics, for example. However, the invention is not limited to this specific application. Indeed, it may be implemented in all sorts of other applications in which it is desirable to use disposable strips on which adjacent zones define a specific utilisation area, these zones after having been used being able, or even having to be (for medical reasons for example) removed from the strip to make room for a following zone. For example, in the medical field, an apparatus of this type could be used for dispensing a series of medical tablets or pills required, in accordance with the dosage prescribed by the doctor, to be taken in a strict order defined in advance. However, the invention is not limited only to applications in the medical field.

The dispensing apparatus according to the invention shown in the FIGS. 2 to 6 comprises a case 20 made of two half shells 20A and 20B, preferably in a moulded plastic material, and assembled to each other along a parting line 21. In the application described, case 20 has an elongated shape and dimensions such that it can easily be held in the palm of an adult's hand.

Figure 2A:
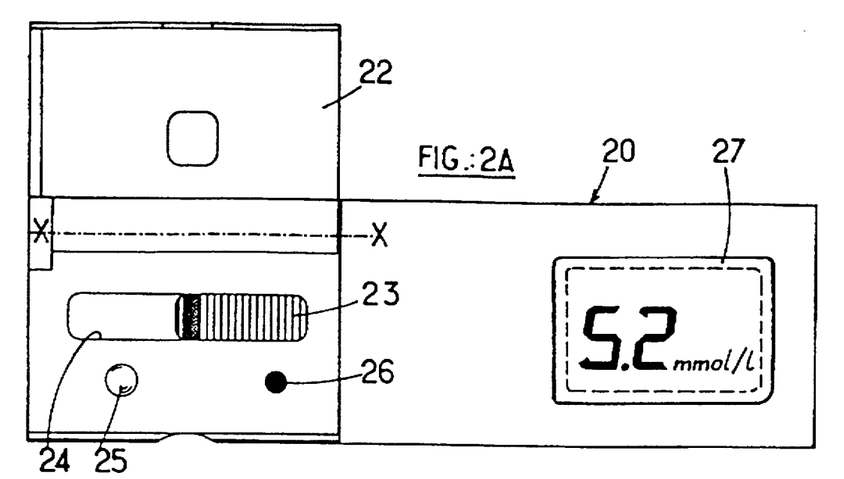
FIGS. 2A, 2B, and 2C are three exterior views, according to three orthogonal planes, of a dispensing apparatus according to the invention.
Figure 2B:
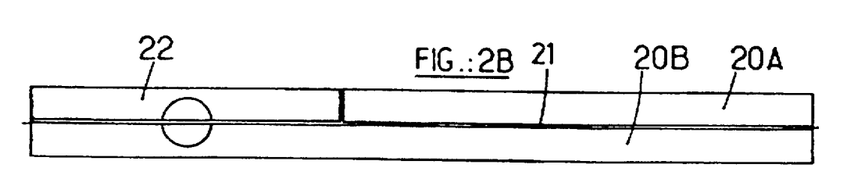
Figure 2C:
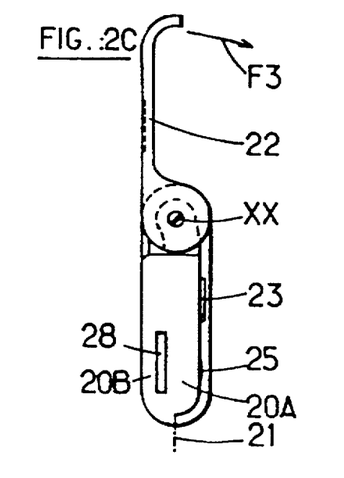

The apparatus comprises a cover 22 extending over part of its length and which is hinged onto case 20 about a longitudinal axis X—X.

In FIGS. 2A and 2C, cover 22 has been shown in an open position, so that one can see a button 23 sliding in a guide 24 arranged in upper half shell 20A of case 20. A small magnifying lens 25 enables a part of the disposable strip (not shown here) which is slid inside the apparatus to be observed. A push button 26 is intended to recall previously taken measurements stored in the memory of the apparatus, for display on a display 27 also used to enable the results of the measurement which has just been made to be read immediately.

It is to be noted that the apparatus is switched on as soon as button 23 is activated and its power supply (preferably an incorporated battery) is switched off after the lapse of a predetermined period of time (60 seconds for example) defined from the moment when any manipulation of the apparatus by the user has ceased.

From the side of cover 22, on the lateral narrow edge of case 20, the apparatus has an opening 28 which is the mouth of a circulation passage 29 (FIG. 3) of the disposable strips.

Figure 3:
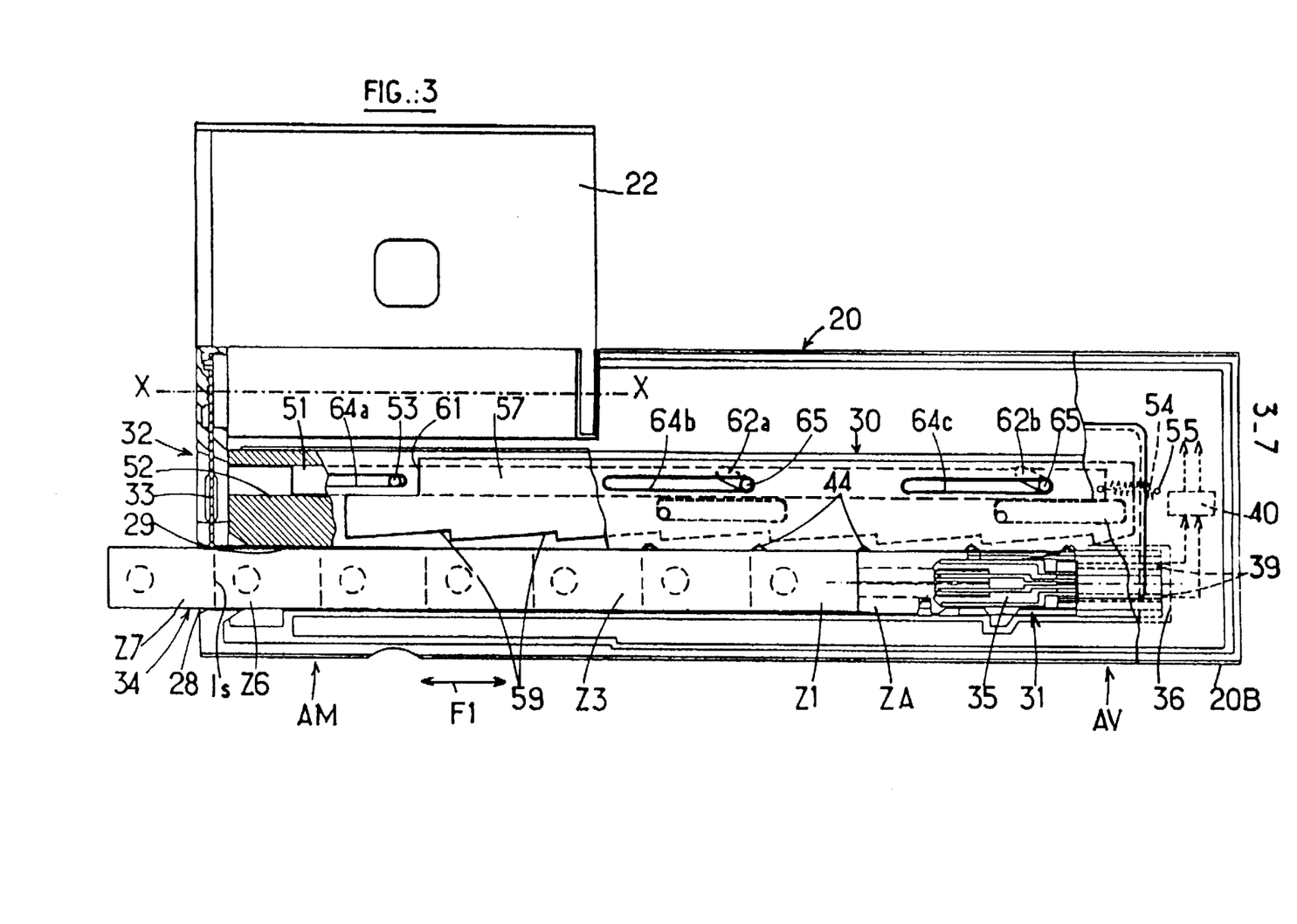
FIG. 3 is a plane view of a dispensing apparatus according to the invention, the upper part of its case being assumed to have been removed and certain parts of it being shown partially cut away.

FIG. 3 shows the dispensing apparatus according to the invention with upper half shell 20A having been removed. Consequently, several operating units can be observed, and in particular:

- a forward feed mechanism 30 which more particularly forms the subject of the invention enables a disposable strip to be fed step by step into passage 29 via the repeated action of sliding button 23;
- a sliding unit 31, which is intended to be coupled to a disposable strip and slides into passage 29;
- a cutting unit 32 situated along the lateral narrow edge of the apparatus and comprising a blade 33 mounted so as to slide in a perpendicular direction to axis X—X; and
- a disposable strip 34 having seven measuring zones Z1 to Z7 and a zone ZA forming a leader zone of the strip and enabling it to be coupled to sliding unit 31.

Figure 4:
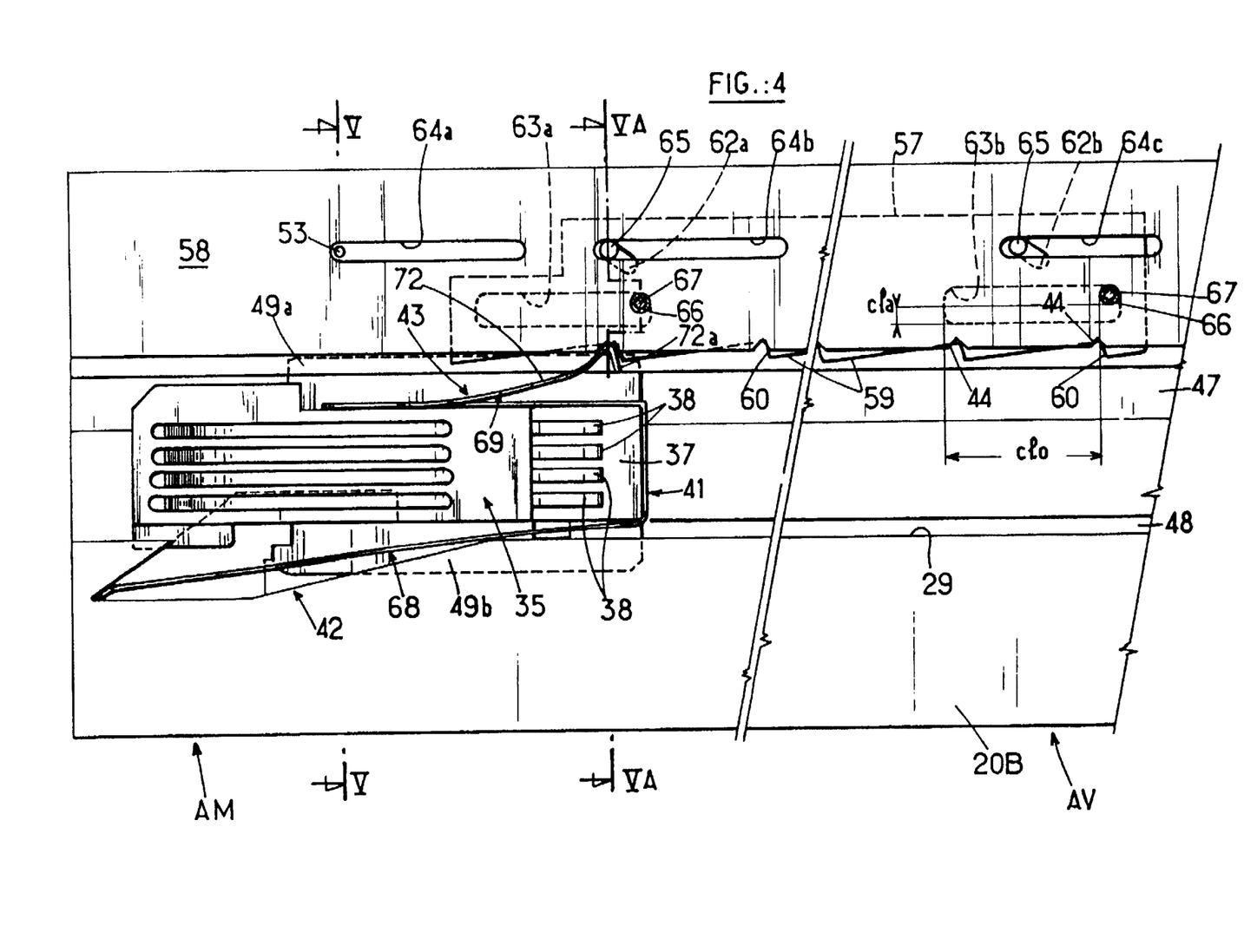
FIG. 4 is a larger scale plane view of the apparatus according to the invention, to illustrate its essential features and in particular the configuration of the forward feed mechanism.
Figure 5:
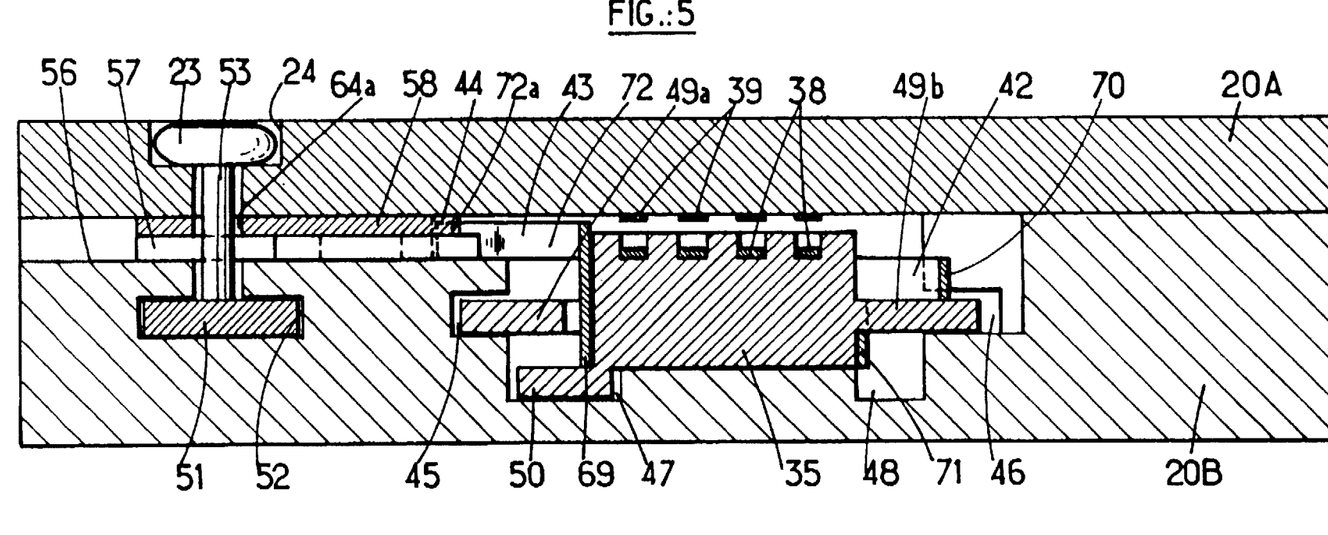
FIGS. 5 and 5A are cross-sectional views taken respectively along lines V—V and VA—VA of FIG. 4.
Figure 5A:
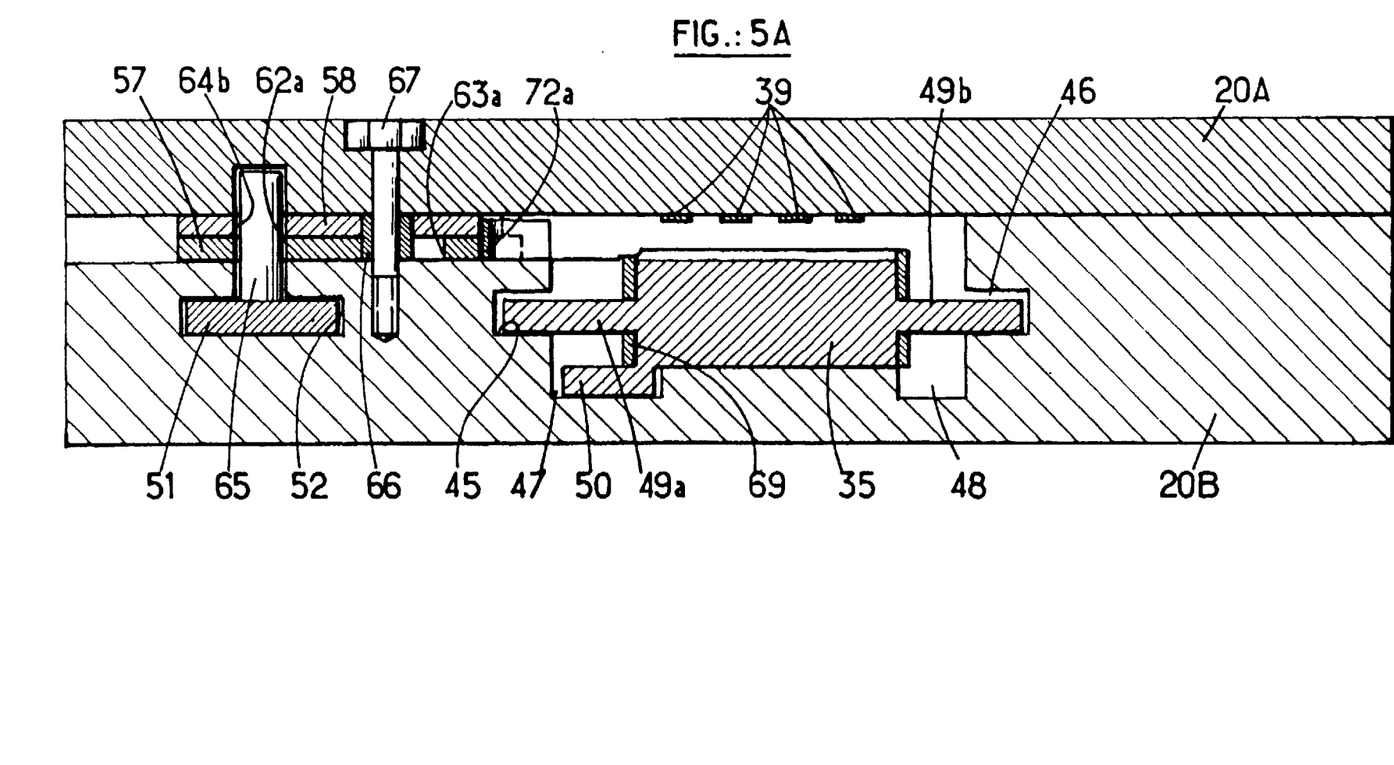
Figure 6:
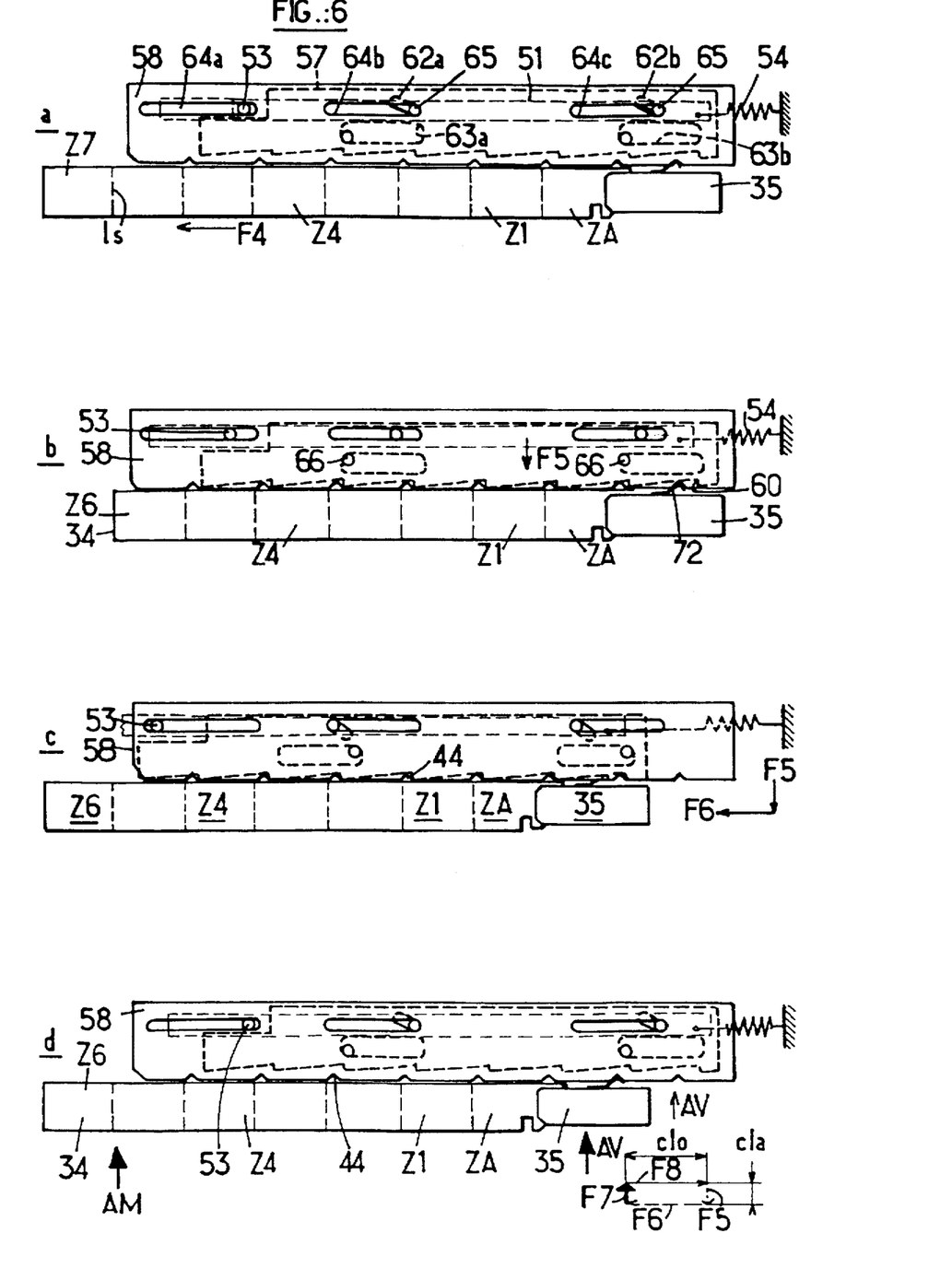
FIG. 6 shows in four views, the kinematics of the forward feed means used in the apparatus according to the invention.

Reference will now be made to FIGS. 4 to 6 in order to describe more specifically the features of the present invention which concern to forward feed mechanism 30.

Sliding unit 31 comprises a cursor 35 capable of circulating in passage 29 which is blocked at its end 36 opposite opening 28. This end will be referred to below as "downstream end" AV in view of the movement of introduction of strip 34 into passage 29. Likewise, the opposite end, close to opening 28 will be called "upstream end" AM. These terms will also be used for the disposable strip, its downstream end thus being situated close to leader zone ZA.

Cursor 35 comprises a cursor body 37 (FIG. 4) carrying electric transmission means 38 for assuring the pick up of electric signals from strip 34 and the transmission of these signals to contact strips 39 which run along the upper wall of passage 29. According to an alternative embodiment this transmission can be achieved via a flexible flat cable which extends into passage 29. Contact strips 39 are connected to an electronic processing circuit 40 (FIG. 3) which is in turn connected to display 27.

Body 37 also carries resilient blocking and coupling means 41 which co-operate with cam and stop forming means 42 which are in one piece with lower half shell 20B of case 20.

Body 37 further comprises driving and positioning means 43 intended to co-operate with forward feed means 30 and with indexing catches 44 which are provided along passage 29 and respectively define the measuring positions of strip 34.

In FIGS. 4, 5 and 5A in particular one sees that guiding passage 29 has two lateral longitudinal grooves 45, 46 and two longitudinal grooves 47 and 48 arranged in its bottom. Body 37 is of a general parallelepipedal shape from which two lateral ribs 49a and 49b protrude, respectively fitting into lateral grooves 45 and 46 and a lower rib 50 which fits into groove 47 provided in the bottom of passage 29.

According to the invention, forward feed means 30 comprise a bar 51 of rectangular section mounted freely in a longitudinal groove 52 of reverse T-shaped section provided in half shell 20B. This bar 51 is attached to a first rod 53 protruding from groove 52 and passing through half shell 20A to be driven into sliding button 23.

Bar 51 is permanently drawn in direction AV via a return spring 54, housed upstream side, in groove 52 (FIG. 3). This spring 54 is fixed via one of its ends onto bar 51, while its opposite end is fixed onto a small spigot 55 in one piece with half shell 20B and situated at the downstream end of groove 52.

A part of the upper surface of half shell 20B forms a sliding surface 56 extending along passage 29. It acts as support to a ratchet bar 57 intended to slide in a reciprocating manner along the direction of the double arrow F1.

This ratchet bar 57 is caught between sliding surface 56 and an elongated guiding plate 58 disposed above ratchet bar 57 and attached to half shell 20B. It is to be noted that positioning catches 44 for sliding unit 31 are provided in the edge of this guiding plate.

The edge of ratchet bar 57 running along passage 29 has a serrated edged toothing 59, the short flank 60 of each tooth being situated on downstream side AV.

The number of teeth of this toothing is equal to the number of zones provided on a disposable strip 34 having the maximum length acceptable to the apparatus. It is to be noted that the latter can accept disposable strips of any length between this maximum length and that corresponding to a minimum number of zones which it is reasonably useful to provide on the disposable strip (in theory, one could provide only one zone on the strip).

Ratchet bar 57 also has:

a front cut 61 (FIG. 3) extending in the lengthways direction of the bar, above the T-shaped opening 52 of the groove for enabling in particular the movement of rod 53 when button 23 is actuated;

two cuts 63a and 63b having the shape of an oblong opening placed obliquely with respect to the general longitudinal direction of the bar, that is to say, to the direction of double arrow F1; and two rectangular shaped slots 62a and 62b acting as guides for ratchet bar 57.

Guiding plate 58 has three elongated slots 64a, 64b and 64c, aligned on top of each other in the longitudinal direction, thus in the direction of double arrow F1.

Rod 53 which has already been mentioned, passes through the first of these slots 64a. Driving rods 65 pass through the second 64b and third 64c slots and also through oblong openings 62a and 62b of ratchet bar 57. The slots are fixed onto bar 51 and thus move simultaneously with button 23.

Sleeves 66 forming following members, which act as distance sleeves and through which tightening screws 67 screwed into half shell 20B also pass, pass through cuts 63a and 63b.

The length of cuts 63a and 63b define the longitudinal travel clo of the ratchet bar, while their width determines its lateral travel cla (FIG. 4). In this way, cuts 63a and 63b in co-operation with sleeves 66 assure the definition of the movement of bar 57 along an orbital path having a rectangular outline.

Resilient blocking and coupling means 41 and driving and positioning means 43 are preferably made in a same spring plate 57. The latter is U-shaped and may for example be compound filled with the plastic material when cursor 35 is moulded. The central branch 58 of the U is applied against the downstream face of cursor 35 while its lateral branches 59 and 60 extend towards opening 28 of passage 29 running respectively along the lateral sides of cursor 35.

Branch 68 comprises two springs 70 and 71 intended to assure the blocking of cursor 35 in upstream position AM and to release it as soon as a disposable strip is inserted in passage 29. Since this aspect of the apparatus does not form part of the invention, it will not be described in more detail here.

On the other hand, branch 69 plays an important role in the implementation of the invention. It in fact constitutes driving and positioning means 43 which have already been mentioned. It comprises a spring 72 extending downstream and ending in a hook 72a. The latter is intended to co-operate with catches 44 and also with toothing 59 of ratchet bar 57.

It will be noted that the edges of the disposable strip do not comprise any notches or other elements necessary to drive the strip. Indeed, as a result of the particular characteristics of the invention, this driving is assured exclusively via cursor 35 on which forward feed mechanism 31, which has just been described, acts. The shape of the disposable strip is thus very simple.

In FIG. 3, the apparatus has been shown when the user has just inserted a disposable strip into it. However, the strip has not yet entirely reached the end of passage 29. For this to happen, the (fictitious) line of separation ls between zones Z7 and Z6 must be placed before the cutting edge of cutting unit 32. The forward feed mechanism is inoperative; ratchet bar 57 is thus in its downstream position, its toothing 59 being outside passage 29.

On the contrary, in FIG. 4, cursor 35 is in the extreme upstream position in passage 29 with no strip being present in the apparatus. However, one assumes in this figure that the user has just manoeuvred button 23 for the last time, that leader zone ZA has already been ejected from the apparatus, but that the user has not yet released button 23. Consequently, in this configuration, ratchet bar 57 is still in its position AM, return spring 54 is taut and short flank 60 of the most upstream tooth of toothing 59 is still engaged with hook 72a of spring 72. Furthermore, rod 53 engaged in button 23 is at the downstream end of groove 64a of guiding plate 58.

The four views a to d of FIG. 6 show the main positions of the components of the apparatus according to the invention during a complete forward feed cycle of the disposable strip.

More precisely, in FIG. 6a and as compared to FIG. 3, disposable strip 34 is completely inserted in the apparatus, cursor 35 being thus at the end of travel at the downstream end of passage 29.

Spring 54 holds ratchet bar 57 in the downstream position and due to the obliquity of slots 62a and 62b, this bar occupies the external lateral position in relation to passage 29.

Zone Z7 of the strip which then protrudes from the apparatus, may thus be used for a sugar level measurement.

When the user has finished this measurement, he closes cover 22 at the same time cutting zone Z7 along separation line ls with zone Z6.

The user must then make zone Z6 come out of the apparatus when using it again. In order to do this, he opens cover 22, then actuates button 23 in the direction of arrow F4 (FIG. 6b). The result of this is firstly the configuration of the components shown in this figure, a configuration which is only transitory, but which shows that ratchet bar 57 moves first laterally inwards in the direction of arrow F5 on travel cla, again due to the obliquity of slots 62a and 62b. Toothing 59 is then placed in the active region of spring 72.

Since button 23 continues to be pushed forward, the most downstream flank 60 of toothing 59 then comes into contact with hook 72a of spring 72, against the force of return spring 54, then this hook exerts a driving force on cursor 35. The latter thus moves towards upstream end AM of passage 29 pushing disposable strip 34 in front of it (in the direction of arrow F6).

The movement in this direction stops, when travel clo is completed, that is to say when the downstream edges of cuts 63a and 63b come into contact with sleeves 66 which are engaged around screws 67. Since this travel corresponds exactly to the length of a zone on disposable strip 34, zone Z6 is thus outside the apparatus.

The user then has only to release button 23 which brings ratchet bar 57 towards its starting position via the action of spring 54 and along the travel symbolised by arrows F7 and F8 in FIG. 6d. Furthermore, since hook 72a of spring 72 with which cursor 37 is provided, is placed in indexing catch 44 corresponding to zone Z6 of the disposable strip, the latter remains stable in its new position.

One thus sees that this operating cycle involves an orbital movement of the ratchet bar along an outline which has a closed rectangular curve along the direction of arrows F5 to F8 shown in FIG. 6.

Of course, this cycle may be repeated for all the measuring zones of disposable strip 34, until only leader zone ZA is left in the apparatus. However, in the corresponding position of cursor 35, this zone is uncoupled from the latter and the user may thus easily remove it from the apparatus so as to be able to introduce a new disposable strip.

What is claimed is:

1. A dispensing apparatus requiring the use of disposable elements having the shape of strips to operate, each of these strips comprising in the longitudinal direction several successive utilization zones adapted to be detached from the strip after their use, said apparatus comprising:

a case defining a circulation passage for said strips, said passage having, taking account of the direction in which said strips are introduced, an upstream end and a downstream end;

a forward feed mechanism for bringing said strip out of the circulation passage in accordance with a step by step movement after its introduction into the circulation passage by a user;

a sliding unit, mounted so as to move in said passage, operationally coupled to said forward feed mechanism and adapted to be coupled to the downstream end of said strip when it is introduced by the user; and coupling means carried by said sliding unit and arranged so as to assure the coupling between the latter and said strip;

said sliding unit comprising a cursor mounted so as to slide in said circulation passage and provided with a driving member, said forward feed mechanism comprising ratchet means adapted to co-operate with said driving member to assure said coupling and to enable the step by step forward feed of said cursor, and said ratchet means being coupled to a control button mounted freely in said case to enable said step by step movement to be controlled; and wherein said ratchet means comprises a ratchet bar mounted in said case parallel to said circulation passage so as to be able to carry out an orbital movement in its own plane, said ratchet bar having means for, during each orbital movement corresponding to one forward step of said cursor, engaging with said driving member of said cursor.

2. A dispensing apparatus according to claim 1, wherein said orbital movement has a rectangular outline.

3. A dispensing apparatus according to claim 1, wherein said ratchet bar comprises a serrated edged toothing whose teeth are intended to engage with said driving member.

4. A dispensing apparatus according to claim 1, wherein said ratchet bar has at least one cut in which a following member is engaged fixed in relation to said case to define with said cut said orbital movement.

5. A dispensing apparatus according to claim 1, wherein resilient return means are provided for drawing said ratchet bar in the opposite direction to the direction of introduction of said disposable strip into said circulation passage.

6. A dispensing apparatus according to claim 1, 2, 3, 4, or 5, wherein indexing catches are provided in said circulation passage step by step movements, and wherein said driving member is arranged to engage with said indexing catches to fix each position of said cursor.

* * * * *